United States Patent [19]

Rougier et al.

[11] Patent Number: 4,668,664
[45] Date of Patent: May 26, 1987

[54] BI- OR TRI-ENIC FATTY ESTERS OF ERYTHROMYCIN A; PHARMACEUTICAL AND COSMETIC COMPOSITIONS CONTAINING THEM

[75] Inventors: André Rougier, Dammartin En Goele; Didier Dupuis, Le Raincy; Michel Philippe, Antony; Henri Sebag; Didier S. Leger, both of Paris, all of France

[73] Assignee: L'Oreal, Paris, France

[21] Appl. No.: 863,029

[22] Filed: May 14, 1986

[30] Foreign Application Priority Data

May 14, 1985 [FR] France ................. 85 07287

[51] Int. Cl.$^4$ .................. A61K 31/70; C07H 17/08
[52] U.S. Cl. .................. 514/29; 536/72; 424/DIG. 5; 424/47; 424/69; 514/859
[58] Field of Search .............. 514/29; 536/7.2, 7.4

[56] References Cited

U.S. PATENT DOCUMENTS 2,862,921 12/1958 Booth et al. .................. 536/7.2
4,575,497 3/1986 Omura et al. .................. 536/7.4

*Primary Examiner*—Johnnie R. Brown
*Assistant Examiner*—Elli Peselev

*Attorney, Agent, or Firm*—Cushman, Darby & Cushman

[57] ABSTRACT

Linear bi- or tri-enic fatty esters of erythromycin A have the formula

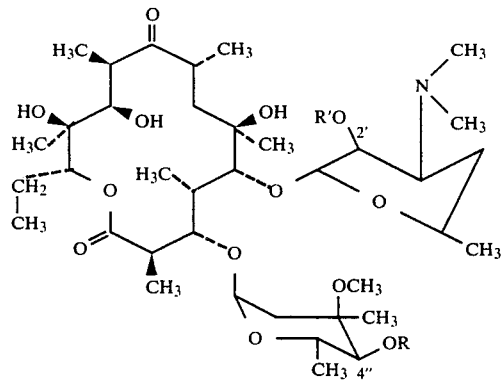

wherein one of R and R' represents a linear bi- or tri-enic $C_{18}$ acyl radical having an all cis (Z) stereochemical configuration and the other of R and R' represents hydrogen.

10 Claims, No Drawings

BI- OR TRI-ENIC FATTY ESTERS OF ERYTHROMYCIN A; PHARMACEUTICAL AND COSMETIC COMPOSITIONS CONTAINING THEM

The present invention relates to new linear bi- or tri-enic fatty esters of erythromycin A, to a process for their preparation and to cosmetic and pharmaceutical compositions containing them for use in the treatment of various dermatoses, principally in the treatment of acne.

More particularly, the present invention relates to the use of the new bi- or tri-enic fatty esters of erythromycin A in the treatment of dermatoses, infectious or not, the origin of which can be bacterial or mycrobacterial, or can be linked to the implantation of certain yeasts having a pathogenic character.

The new bi- or tri-enic fatty esters of erythromycin A are also usefully employed in the prevention of cutaneous infections whose appearance is a secondary phenomenon to any cutaneous stress such as a cut or burn.

The present invention envisions, more particularly, the use of the new bi- or tri-enic fatty esters of erythromycin A in the treatment of acne.

Acne is a cutaneous disorder, polymorph, (several types of lesions existing in the same person), occurring at puberty and spontaneously disappearing in the great majority of cases at the age of about 20-25.

Acne concerns, in persons afflicted therewith, areas rich in sebaceous glands such as the forehead, face, nose, torso and back, which demonstrates a certain dependence of this dermatosis vis-a-vis sebum, a synthesis product of the gland. Acne does not exist without seborrhea.

Although seborrhea is one of the translations of the sudden hormonal flow occurring at puberty, acne does not appear to be linked to any hormonal disorder.

The etiopathogenesis of acne, although not well defined, originates in the formation of a characteristic lesion, the comedon which results from the obstruction of the pilosebaceous canal caused by a dis-keratinization of the infundibulum zone of the canal.

This obstruction has, for a major effect, the modification of the viscosity of the sebum and the physico-chemical characteristics of the medium (pH, oxygen vapor pressure . . .).

This modification permits hypoproliferation of resident cutaneous strains, principally *propionibacterium acnes*, anaerobic or aero-tolerant strain.

Acne does not exhibit in any case an infectious characteristic in the sense where this dermatosis does not correspond to the implantation of a particular pathogenic strain and that it is not transmissible.

Finally, the bacterial hypoproliferation liberates in the medium certain proteases or hyaluronidases, of bacterial origin, which causes a lysis of the follicular sac thus freeing inflammatory compounds in the skin and releasing an inflammatory type reaction of the organism.

If the nature of the inflammatory compounds is presently non determined, their bacterial origin seems to be in little doubt, explaining, thereby, the good therapeutic success, in inflammatory acne, of antibiotic compounds admininstered orally as well as topically.

Among the anitbiotics, erythromycin, principally under the form of erythromycin base, has been recommended. However, it has been observed that its use requires relatively high concentrations in order to obtain a satisfactory result.

Moreover, as recent studies have shown, certain strains of *propionibacterium acnes* exhibit progressive resistance to erythromycin so that this antibiotic, in the form of erythromycin base or in the form of its esters, has found only limited use in anti-acne compositions.

The topical application of erythromycin base or its esters also exhibits a disadvatange due to their unfavorable penetration characteristics across the corneum stratum, thus limiting their efficacy.

However, the new bi- or tri-enic fatty esters of erythromycin A, according to the present invention provide a satisfactory solution to the aforementioned problems encountered in the use of erythromycin base or its esters, since studies carried out have evidenced that these new esters exert a selective activity on the principal germ responsible for inflammations, i.e. *propionibacterium acnes*, all while having a very weak activity vis-a-vis cutaneous germs such as *staphylococcus epidermis*, thereby permitting effective treatment of skin disorders without disturbing the equilibrium of the skin.

Further, these new bi- or tri-enic fatty esters of erythromycin A exhibit significantly improved skin penetration characteristics compared to erythromycin base or its esters and are quite well tolerated by the skin due to the nature of their lipophilic chain which is derived from essential fatty acids.

Additionally, these new bi- or tri-enic fatty esters of erythromycin A have proved to be active vis-a-vis resistant strains of *propionibacterium acnes* which is not the case with other known esters of erythromycin A as has been shown by the comparative studies which are reported below.

These studies have also demonstrated that this selective activity, vis-a-vis resistant strains of *propionibacterium acnes*, is limited to bi- and tri-enic fatty esters of cis stereochemical configuration, the bi- and tri-enic ester of trans stereochemical configuration being less active than saturated or monounsaturated fatty esters.

As background, mention is made of U.S. Pat. No. 2,862,921 which describes the preparation of saturated fatty esters of erythromycin A such as the monostearate of erythromycin A and mono-enic esters such as the monooleate of erythromycin A. These fatty esters are, on oral administration, more agreeable to the taste than erythromycin base.

The present invention relates to linear bi- or tri-enic fatty esters of erythromycin A having the formula

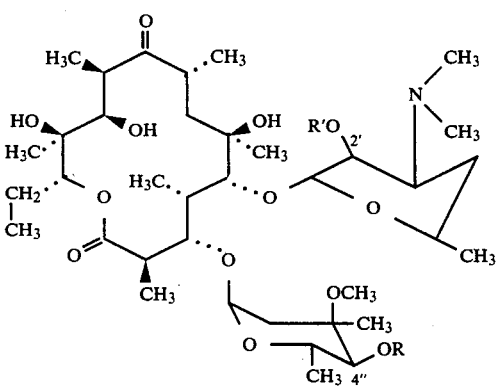

wherein one of R or R' represents linear bi- or tri-enic $C_{18}$ acyl radical having all cis (Z) stereochemical configuration and the other of R' or R represents hydrogen, as well as mixtures and salts of these said esters.

According to a preferred embodiment of the present invention R or R' represents the following radicals:
Z-9, Z-12-octadecadienoyl or linoleoyl,
Z-9, Z-12, Z-15-octadecatrienoyl or α-linolenoyl and
Z-6, Z-9, Z-12-octadecatrienoyl or γ-linolenoyl.

According to a particularly preferred embodiment of the present invention R or R' represents the following radicals:
Z-9, Z-12-octadecadienoyl or linoleoyl and
Z-9, Z-12, Z-15-octadecatrienoyl or α-linolenoyl.

The present invention also relates to a process for preparing the bi- or tri-enic fatty esters of erythromycin A such as defined above.

The esterification reaction is generally carried out by reacting in an anhydrous solvent medium, preferably pyridine, an excess of an acid chloride or an acid anhydride of a $C_{18}$ bi- or tri-enic fatty acid having all cis stereochemical configuration with erythromycin A in the form of base and in the presence of a catalyst, preferably, 4-N,N-dimethylamino pyridine.

In certain instances, the esterification can be oriented in a preferential manner in the 2' or 4" position by an appropriate choice of reactants.

Thus, linoleic acid chloride orients the esterification in the 4" position, whereas linoleic acid anhydride orients the esterification in the 2' position a majority of the time.

If an excess of bi- or tri-enic fatty acid chloride is added relative to the requisite stoichiometric quantity, there are obtained the diesters in the 2' and 4" position which are less active than the mono-esters.

The esterification reaction can also be effected starting with an excess of a bi- or tri-enic $C_{18}$ fatty acid having all cis stereochemical configuration which is transformed in situ into the acid anhydride, in an anhydrous solvent medium, preferably in tetrahydrofuran alone or in admixture with another solvent such as pyridine.

According to this variation of the present invention, the reaction with erythromycin A is carried out in tetrahydrofuran in the presence of a base such as sodium hydrogen carbonate and/or pyridine.

This process orients the esterification, in the majority of instances, in the 2' position of erythromycin A.

The present invention also relates to a pharmaceutical composition which can be administered topically, orally, parenterally or rectally, as well as to a composition having a cosmetic character for the treatment of various dermatoses, principally acne. These compositions are provided in anhydrous form and contain at least one fatty ester of erythromycin A according to the invention and/or a salt thereof at a concentration between 0.1 and 10 weight percent, and preferably between 2 and 6 weight percent based on the total weight of the composition.

For the preparation of compositions according to the invention containing, as the active component, at least one fatty ester of erythromycin A, such as defined above, conventional vehicles or carriers, as well as adjuvants described in the literature for pharmaceutical, cosmetic and related fields can be employed.

For the preparation of solutions, a physiologically acceptable organic solvent can be used.

Representative physiologically acceptable organic solvents include, principally, acetone, isopropyl alcohol, tri-glycerides of fatty acids, glycol ethers, $C_1$-$C_4$ alkyl esters of short chain acids and polytetrahydrofuran ethers.

The compositions according to the present invention can also include a thickening agent, such as cellulose and/or derivatives of cellulose, in an amount ranging from 0.5 to 20 weight percent relative to the total weight of the compositions.

The compositions according to the present invention can also contain, in combination with the fatty ester of erythromycin A, at least one other known anti-acne agent.

If necessary or desirable, a conventional adjuvant such as an anti-oxidant, a preservative, a perfume or a dye can be added. Representative useful anti-oxidants include, for example, t.-butyl hydroxyquinone, butyl hydroxyanisole, butyl hydroxytoluene and α-tocopherol and its derivatives.

The pharmacologic and galenic transformations of the compounds of the present invention are effected in a known manner.

The galenic forms which can be employed for topical application include creams, milks, gels, more or less thick lotions, lotions carried by pads, ointments, sticks or even aerosol formulations provided in the form of sprays or foams.

The compositions for oral administration can be provided in the form of tablets, gelules, lozenges, syrups, suspensions, powder emulsions, granules or solutions.

The compositions can also be provided in the form of suppositories.

The treatment of acne using topical compositions according to the present invention comprises applying a sufficient amount of said composition 2 or 3 times each day on the area of the skin to be treated, this regimen being repeated for a period of time ranging from 2 to 20 weeks, and preferably 4 to 10 weeks.

The compositions according to the present invention can also be used as a preventative, that is to say, they can be applied to an area of the skin which is susceptible of being attacked by acne.

Comparative Studies on the Activity of Fatty Esters of Erythromycin A

The activity of the fatty esters of erythromycin A has been studied by the dilution method so as to determine the Minimal Inhibiting Concentration (MIC). This method is described and employed by G. A. Denys et al, Antimicrobial Agents and Chemotherapy (1983), 23, 335-337 and J. J. Leyden et al, J. Am. Acad. Dermatol. (1983) 8 (1) 41-5, and utilizes as the strain of *propionibacterium acnes*, the P 37 strain furnished by Cunliffe and Holland.

This P 37 strain is the subject of studies described in the following publications:
J. Greenman, K. T. Holland and W. J. Cunliffe, Journal of General Microbiology (1983) 129, 1301-1307,
E. Ingham, K. T. Holland, G. Gowland and W. J. Cunliffe, ibid (1980) 118, 59-65 and
K. T. Holland, J. Greenman and W. J. Cunliffe, Journal of Applied Bacteriology (1979) 47, 383-394.

Selection and Isolation of Sensitive and Resistant Populations

The P 37 strain is sensitive to erythromycin as evidenced by its minimal inhibiting concentration (MIC=0.78 μg/ml).

On the other hand, after 8 successive sub-cultures in the same medium (RCM* 19/20, DMSO 1/20 in volume) so as to obtain a progressive stabilization of this strain in this medium, a progressive resistance to erythromycin is manifested under the following form:

After display of a standardized inoculum (DO=1.8 to 450 nm) on gelose medium (RCM+furazolidone), in a Petri dish, a disc of 9 mm in diameter is deposited in its center. On this disc, 50 μg of erythromycin (in solution in DMSO) are deposited.

*Reinforced Clostridium Medium (OXOID)

After 6 days at 36° C. in an anaerobic medium (GAS-PAK system, B.B.L.) a growth inhibition zone of the strain is clearly visible (total diameter=42 mm), the great majority of the colonies being situated at the periphery of the inhibition zone.

On the other hand, at its interior a few colonies clearly appear.

The two types of colonies are then retained by pulling away from the gelose medium (sterilized platinum loop):

(1) at the interior of the inhibition zone the strains denominated P 37 E⊖ are retained due to their apparent resistance to erythromycin (2) at 1 cm beyond the periphery of the inhibition zone the strains denominated P 37 E⊕ are retained.

After isolation and culture, the strains P 37 E⊕ and P 37 E⊖ show effectively very different sensitivities to erythromycin as illustrated by the following values of their respective MIC values.

|  | MIC (μg/ml) |
|---|---|
| P 37 | 0.78 |
| P 37 E⊕ | 0.78 |
| P 37 E⊖ | 50 |

This phenomenon is confirmed by the IC 50 study (inhibiting concentration at 50%) which represents the concentration of erythromycin where, at a constant culture time, 50% of the survivors among the population are found.

|  | MIC (μg/ml) |
|---|---|
| P 37 | 50 |
| P 37 E⊕ | 5 |
| P 37 E⊖ → | 100 |

The Minimal Inhibiting Concentration (MIC) expressed in μg/ml of the fatty esters of the erythromycin A tested vis-a-vis strains P 37⊕ and P 37⊖ is reported in the following table:

It will be noted that the bi- and tri-enic $C_{18}$ fatty esters of the present invention, having cis configuration, are clearly more active on strain P 37 E⊖ than both the reference fatty esters and erythromycin. This study confirms not only the significance of the nature of the $C_{18}$ fatty chain, but also the cis stereochemical configuration of the double bonds.

In effect, the data appearing in this table show that the $C_{18}$ fatty esters of "trans" stereochemical configuration, i.e. O-linoelaidoyl-2' erythromycin A and O-linoelaidoyl-4" erythromycin A, are less active vis-a-vis the P 37 E⊖ strain.

The following examples illustrate the preparation of bi- and tri-enic $C_{18}$ fatty esters of erythromycin A according to the present invention, as well as pharmaceutical or cosmetic compositions in the treatment of dermatoses and, principally, acne.

Preparation of Bi- and Tri-Enic $C_{18}$ Fatty Esters of Erythromycin A in Accordance with the Invention Example 1—First Process for the Preparation of O-linolenoyl-2'-erythromycin A In a round bottom flask under an inert atmosphere are dissolved 740 mg (1.36 mmol) of linoleic anhydride and a catalytic amount (3 mg; 0.02 mmol) of 4-N,N-dimethylamino pyridine in 6 ml of anhydrous pyridine. To the solution there are added 200 mg (0.27 mmol) of erythromycin A and the resulting reaction mixture is stirred for 8 hours at 20° C. (the course of the reaction is monitored by thin layer silica gel chromatography; eluant - 90:10 methylene chloride/methanol). The solution is then poured into 40 ml of bicarbonated water, then extracted with ethyl acetate. The organic phase is dried on magnesium sulfate, filtered and then concentrated under a partial vacuum. The resulting crude product is chromatographed on a silica gel column (HPLC) by using as the eluant a 98:2 mixture of methylene chloride/methanol. After evaporation of the solvent 190 mg (70% yield) of pure O-linoleoyl-2' erythromycin A are isolated.

Melting point: 79°–80° C. (after recrystallization in an ethylacetate/hexane mixture).

$[\alpha]_D^{20} = -55°$ (C=13 mg/ml methylene chloride).

| Analysis: $C_{55}H_{97}NO_{14}$; MW = 996.4 | | | |
|---|---|---|---|
|  | C | H | N |
| Calculated, % | 66.3 | 9.81 | 1.4 |
| Found, % | 66.32 | 9.86 | 1.4 |

| Esters of Erytrhomycin A | Stereochemical Configuration | Reference | P 37 E⊕ (sensitive) | P 37 E⊖ (resistant) |
|---|---|---|---|---|
| O—linolenoyl-2' | (Z-9, Z-12) | (1) | 4 | 16 |
| O—linoleoyl-4" | (Z-9, Z-12) | (1) | 3.5 | 28 |
| O—α-linolenoyl-4" | (Z-9, Z-12, Z15) | (1) | 4.5 | 37 |
| O—stearoyl-2' | saturated | (2) | <1.56 | >50 |
| O—oleoyl-2' | (Z-9) | (2) | 50 | 100 |
| O—linoelaidoyl-2' | (E-9, E-12) | (3) | 25 | 100 |
| O—linoelaidoyl-4" | (E-9, E-12) | (4) | 25 | 100 |
| O—arachidonoyl-2' | (Z-5, Z-8, Z-11, Z-14) | (5) | 6.25 | >50 |
| Control: |  |  |  |  |
| Erythromycin |  |  | 0.78 | >50 |

(1) Esters according to the invention - see Examples of preparation 1-3.
(2) Esters for comparison (see preparation of Examples 4 and 5 in U.S. Pat. No. 2,862,921)
(3) Ester for comparison - see Example 4 below
(4) Ester for comparison - see Example 5 below
(5) Ester for comparison - see Example 6 below.

Infra red - significant band at 1.730 cm$^{-1}$ (ester).
NMR of $^{13}$C(CDCl$_3$ 3 ref. internal TMS).

γ negative effect (−2 ppm) at 1' and 3' positions indicating esterification in 2' position. Characteristic displacements of the linoleoyl chain and confirmation of the two cis (Z) double bonds.

Mass spectrometry (I.C.).

The spectrum confirms the presence of the linoleoyl chain and the site of esterification.

Second Process for the Preparation of O-linoleoyl-2' Erythromycin A

In a round bottom flask under an inert atmosphere are dissovled 50 g of linoleic acid (178 mmols) in 300 ml of anhydrous tetrahydrofuran. To the reaction mixture, cooled to 0° C., there are added 10 ml of anhydrous pyridine and 17.3 ml of ethyl chloroformate (180 mmols). After 15 minutes of stirring, 90 g of sodium hydrogen carbonate (1.07 mol) are added and then 50 g of erythromycin A (68 mmols) previously dissolved in 700 ml of tetrahydrofuran. The reaction mixture is then left under stirring for 15 hours whereby the temperature rises to ambient temperature (the reaction is followed by thin layer silica gel chromatography; eluant - 90:10 methylene chloride/methanol). The solution is poured into a 1:1 mixture of ethanol/ammoniated water and extracted with heptane. The organic phase is dried on magnesium sulfate, filtered and then concentrated under a partial pressure. The resulting crude product is chromatographed on a silica gel column (HPLC) by using as the eluant a 7:5 mixture of ethyl acetate/hexane. After evaporation of the solvent, 50 g (yield -74%) of O-linoleoyl-2' erythromycin A whose characteristics are identical to those of the compound obtained by the first process given above are isolated.

Example 2—Preparation of O-linoleoyl-4'' erythromycin A

In a round bottom flask under an inert atmosphere are dissolved 5.9 g (10.8 mmols) of linoleoyl chloride and a catalytic amount (5 mg, 0.033 mmol) of 4-N,N-dimethylamino pyridine in 25 ml of anhydrous pyridine. There are then added 2 g (2.7 mmols) of erythromycin A to the solution and the resulting reaction mixture is stirred for 8 hours at 20° C. (reaction followed by C.C.M. on silica gel; eluant - 90:10 dichloromethane/methanol).

After the end of the reaction, the solution is poured into 60 ml of bicarbonated water, then extracted with ethyl acetate. The organic phase is dried on magnesium sulfate, filtered and then concentrated under a partial vacuum. The resulting crude product is chromatographed on a silica gel column (HPLC) by using as the eluant a 98:2 mixture of dichloromethane/methanol.

After evaporation of the solvent 1.7 g (yield -62%) of pure O-linoleoyl-4'' erythromycin A are isolated.

Melting point: 81°-83° C. (ethylacetate/hexane).
$[\alpha]_D^{20} = -52°$ (C=35 mg/ml dichloromethane).

| Analysis: C$_{55}$H$_{97}$NO$_{14}$; MW = 996.4 | | | |
|---|---|---|---|
| | C | H | N |
| Calculated, % | 66.3 | 9.81 | 1.4 |
| Found, % | 66.35 | 9.85 | 1.43 |

Infra red - significant band at 1.730 cm$^{-1}$.
NMR of $^{13}$C (CDCl$_3$, ref. internal T.M.S.).

Negative γ effect at 5''(-2 ppm) indicating the site of esterification. Characteristic displacements of the linoleoyl chain and confirmation of the two cis (Z) double bonds.

Example 3—Preparation of O-α-linolenoyl-4'' erythromycin A

In a round bottom flask under an inert atmosphere are dissolved 5.9 g (10.8 mmols) of linolenic anhydride and a catalytic amount (5 mg, 0.033 mmol) of 4-N,N-dimethylamino pyridine in 25 ml of anhydrous pyridine. There are then added 2 g (2.7 mmols) of erythromycin A to the solution and the resulting mixture is stirred for 8 hours at 20° C. (reaction is followed by CCM on silica gel; eluant - 90:10 mixture of dichloromethane/methanol).

The solution is poured into 60 ml of bicarbonated water and then extracted with ethyl acetate. The organic phase is dried on magnesium sulfate, filtered and then concentrated under a partial vacuum. The resulting crude product is chromatographed on a silica gel column (HPLC) by using as the eluant a 98:2 mixture of dichloromethane/methanol.

Melting point: 68°-71° C. (ethylacetate/hexane).
$[\alpha]_D^{20} = -58°$ (C=12 mg/ml dichloromethane).

| Analysis: C$_{55}$H$_{95}$NO$_{14}$.3H$_2$O; MW = 1048.4 | | | |
|---|---|---|---|
| | C | H | N |
| Calculated, % | 63.03 | 9.62 | 1.34 |
| Found, % | 63.1 | 9.31 | 1.46 |

Infra red - significant band at 1.730 cm$^{-1}$ (ester).
NMR of $^{13}$C (CDCl$_3$, ref. internal TMS).

Negative γ effect in position 5'' (−2 ppm) indicating the site of esterification; characteristic displacements of the linolenoyl chain and confirmation of the 3 cis (Z) double bonds.

Preparation of Fatty Esters of Erythromycin A for Comparison

Example 4—Preparation of O-linoelaidoyl-2' erythromycin A

In a round bottom flask, under an inert atmosphere, are dissolved 5.9 g (10.8 mmols) of linoelaidic anhydride and a catalytic amount (5 mg, 0.03 mmol) of 4-N,N-dimethylamino pyridine in 25 ml of anhydrous pyridine. There are then added 2 g (2.7 mmols) of erythromycin A to the solution, the resulting reaction mixture being stirred for 8 hours at 20° C. (reaction is followed by CCM on silica gel; eluant - 90:10 dichloromethane/methanol).

The solution is poured into 60 ml of bicarbonated water and then extracted with ethyl acetate. The organic phase is dried on magnesium sulfate, filtered and then concentrated under a partial vacuum. The resulting crude product is then chromatographed on a silica gel column (HPLC) by using as the eluant a 98:2 mixture of dichloromethane/methanol.

After evaporation of the solvent 1.85 g (68% yield) of O-linoelaidoyl-2' erythromycin A are isolated.

Melting point: 54°-56° C. (ethylacetate/hexane).
$[\alpha]_D^{20} = -53°$ (C=10 mg/ml dichloromethane).

| Analysis: $C_{55}H_{97}NO_{14}$; MW = 996.4 | | | |
|---|---|---|---|
| | C | H | N |
| Calculated, % | 66.3 | 9.81 | 1.4 |
| Found, % | 66.15 | 9.8 | 1.51 |

Infra red - significant band at 1.730 cm $^{-1}$ (ester).
NMR of $^{13}C$ (CDCl$_3$, ref. internal TMS).

Negative γ effects in 1' (−2.1 ppm) and 3' (−1.5 ppm) positions indicating the site of esterification; confirmation of the two trans double bonds (E).

Example 5—Preparation of O-linoelaidoyl-4' erythromycin A

This compound is isolated during the chromatography of the crude product obtained in Example 4. (Initial elution fractions).

After evaporation of the solvent 220 mg (8% yield) of O-linoelaidoyl-4" erythromycin A are isolated.

Melting point: 57°-59° C. (ethylacetate/hexane).
$[\alpha]_D^{20} = -51°$ (C=22 mg/ml dichloromethane).

| Analysis: $C_{55}H_{97}NO_{14}$; MW = 996.4 | | | |
|---|---|---|---|
| | C | H | N |
| Calculated, % | 66.3 | 9.81 | 1.4 |
| Found, % | 66.16 | 9.8 | 1.51 |

Infra red - significant band at 1730 cm$^{-1}$ (ester).
NMR of $^1H$ (CDCl$_3$, ref. internal TMS).
Confirmation of the two trans double bonds (E).

Example 6—Preparation of O-arachidonoyl-2' erythromycin A

In a round bottom flask, under an inert atmosphere, are dissolved 6.4 g (10.8 mmols) of arachidonic anhydride and a catalytic amount (5 mg, 0.033 mmol) of 4-N,N-dimethylamino pyridine in 25 ml of anhydrous pyridine. There are then added 2 g (2.7 mmols) of erythromycin A to the solution and the resulting reaction mixture is stirred for 8 hours at 20° C. (reaction is followed by CCM; eluant - 90:10 mixture of dichloromethane/methanol). The solution is poured into 60 ml of bicarbonated water and then extracted with ethyl acetate. The organic phase is dried on magnesium sulfate, filtered and then concentrated under a partial vacuum. The resulting crude product is chromatographed on a silica gel column (HPLC) by using as the eluant a 98:2 mixture of dichloromethane/methanol.

After evaporation of the solvent 1.67 g (60% yield) of pure O-arachidonoyl-2' erythromycin A are isolated.
$[\alpha]_D^{20} = -53°$ (C=15 mg/ml dichloromethane)

| Analysis: $C_{57}H_{97}NO_{14}$; MW = 1020.36 | | | |
|---|---|---|---|
| | C | H | N |
| Calculated, % | 67.09 | 9.58 | 1.37 |
| Found, % | 67.05 | 9.61 | 1.31 |

Infra red - band at 1730 cm$^{-1}$ (ester).
NMR of $^{13}C$ (CDCl$_3$, ref. internal TMS).

Negative γ effects in 1' (−2.1 ppm) and 3' (−1.8 ppm) positions indicating the position of the ester is in the 2' position.

Characteristic displacements of the arachidonic chain and confirmation of the 4 cis (Z) double bonds.

| Cosmetic and Pharmaceutical Compositions | |
|---|---|
| Gels for the topical treatment of acne | |
| 1. Hydroxy propyl cellulose | 1.5 g |
| Urea | 5 g |
| O—linoleoyl-2'erythromycin A | 2.7 g |
| Isopropanol, sufficient amount for | 100. g |
| 2. Hydroxy propyl cellulose | 1.5 g |
| Ethyl lactate | 10 g |
| O—linoleoyl-4"erythromycin A | 3 g |
| Isopropanol, sufficient amount for | 100 g |
| 3. Hydroxypropyl cellulose | 1 g |
| Urea | 5 g |
| 2,5-di-tert.butyl p-cresol | 0.02 g |
| O—α-linolenoyl-4"erythromycin A | 5 g |
| Isopropanol, sufficient amount for | 100 g |
| Lotions for the Topical Treatment of Acne | |
| 1. Isopropanol | 46 g |
| O—α-linolenoyl-4"erythromycin A | 4 g |
| Triglycerides of $C_8$-$C_{12}$ fatty acids | 50 g |
| 2. Isopropanol | 49.9 g |
| Ethyl lactate | 10 g |
| O—linoleoyl-2'erythromycin A | 0.1 g |
| Triglycerides of $C_8$-$C_{12}$ fatty acids | 40 g |
| 3. Isopropanol | 38 g |
| Acetone | 10 g |
| O—linoleoyl-4"erythromycin A | 2 g |
| Ethyl lactate | 10 g |
| Triglycerides of $C_8$-$C_{12}$ fatty acids | 40 g |
| 4. Isopropanol | 38 g |
| Acetone | 10 g |
| O—linoleoyl-2'erythromycin A | 2 g |
| Dimethyl ether of polytetrahydrofuran (viscosity, 22 centipoises) having the formula $CH_3O$-$[(CH_2)_2$—$CH_2$—$CH_2$—$O]_n CH_3$ wherein n ≅ 5 | 20 g |
| Triglycerides of $C_8$-$C_{12}$ fatty acids | 30 g |
| Stick for the Topical Treatment of Acne | |
| White petrolatum | 51.5 g |
| Petrolatum oil | 15 g |
| Raffinated paraffin | 32 g |
| O—linoleoyl-2'erythromycin A | 1.5 g |
| Suppository (composition per unit) | |
| O—linoleoyl-2'erythromycin A | 0.1 g |
| Triglycerides of caprylic and capric acids | 0.2 g |
| Semi-synthetic glycerides, sufficient amount for | 2 g |

What is claimed is:

1. A linear bi- or tri-enic fatty ester of erythromycin A having the formula

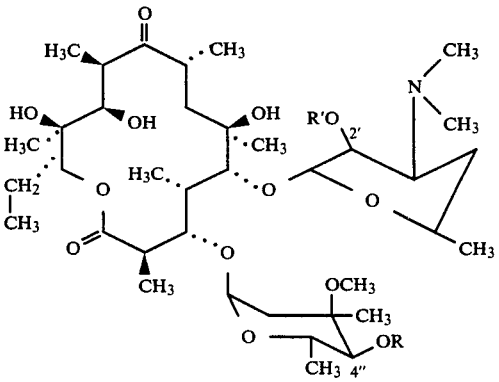

wherein one of R and R' represents a linear bi- or trienic $C_{18}$ acyl radical having an all cis (Z) stereochemical configuration and the other of R and R' represents hydrogen; and the salts therof.

2. The linear bi- or tri-enic fatty ester of claim 1 wherein R or R' represents

Z-9,Z-12-octadecadienoyl or linoleoyl,
Z-9,Z-12,Z-15-octadecatrienoyl or α-linolenoyl and
Z-6,Z-9,Z-12-octadecatrienoyl or γ-linolenoyl.

3. The linear bi- or tri-enic fatty ester of claim 1 selected from
1' O-linolenoyl-2' erythromycin A,
1' O-linolenoyl-4" erythromycin A and
1' O-α linolenoyl-4" erythromycin A.

4. A pharmaceutical composition for the treatment of dermatoses comprising in an anhydrous vehicle an effective amount of the linear bi- or tri-enic fatty ester of erythromycin A of claim 1.

5. The composition of claim 4 wherein said ester is present in an amount ranging from 0.1 to 5 weight percent based on the total weight of said composition.

6. The composition of claim 4 wherein said ester is present in an amount ranging from 2 to 3 weight percent based on the total weight of said composition.

7. The composition of claim 4 wherein said vehicle is acetone, isopropyl alcohol, triglycerides of fatty acids, glycol ethers, $C_1$-$C_4$ alkyl esters of short chain acids, polytetrahydrofuran ethers, or a mixture thereof.

8. The composition of claim 4 which also contains a thickening agent present in an amount ranging from 0.5 to 20 weight percent based on the total weight of said composition.

9. The composition of claim 8 wherein said thickening agent is cellulose or hydroxypropyl cellulose.

10. The composition of claim 4 which also contains an antioxidant, a preservative, a perfume, or dye.

* * * * *

UNITED STATES PATENT AND TRADEMARK OFFICE
CERTIFICATE OF CORRECTION

PATENT NO. : 4,668,664
DATED : May 26, 1987
INVENTOR(S) : ROUGIER et al

It is certified that error appears in the above-identified patent and that said Letters Patent is hereby corrected as shown below:

Col. 6, line 22, "O-linolenoyl-2'-erythromycin A" should read --O-linoleoyl-2'-erythromycin A--.

Col. 11, line 6, "1'O-linolenoyl-2' erythromycin A" should read --1'O-linoleoyl-2' erythromycin A--;

line 7, "1'O-linolenoyl-4" erythromycin A" should read --1'O-linoleoyl-4" erythromycin A--.

Signed and Sealed this

Twenty-ninth Day of March, 1988

Attest:

DONALD J. QUIGG

Attesting Officer     Commissioner of Patents and Trademarks

UNITED STATES PATENT AND TRADEMARK OFFICE
CERTIFICATE OF CORRECTION

PATENT NO. : 4,668,664
DATED : May 26, 1987
INVENTOR(S) : Rougier, et al

It is certified that error appears in the above-identified patent and that said Letters Patent is hereby corrected as shown below:

Column 5, in the table below line 50, the first compound under the heading "Esters of Erythromycin A" should read --0-linoleoyl-2'--.

Signed and Sealed this

Fifteenth Day of November, 1988

*Attest:*

DONALD J. QUIGG

*Attesting Officer*   Commissioner of Patents and Trademarks